(12) United States Patent
Wang et al.

(10) Patent No.: US 8,758,633 B1
(45) Date of Patent: Jun. 24, 2014

(54) DIELECTRIC SPECTROMETERS WITH PLANAR NANOFLUIDIC CHANNELS

(75) Inventors: Pingshan Wang, Central, SC (US); Chunrong Song, Clemson, SC (US)

(73) Assignee: Clemson University, Clemson, SC (US)

( * ) Notice: Subject to any disclaimer, the term of this patent is extended or adjusted under 35 U.S.C. 154(b) by 927 days.

(21) Appl. No.: 12/838,687

(22) Filed: Jul. 19, 2010

Related U.S. Application Data

(60) Provisional application No. 61/229,127, filed on Jul. 28, 2009.

(51) Int. Cl.
*B44C 1/22* (2006.01)

(52) U.S. Cl.
USPC .................. 216/2; 216/83; 216/99; 977/888; 137/833

(58) Field of Classification Search
None
See application file for complete search history.

(56) References Cited

U.S. PATENT DOCUMENTS

| | | | |
|---|---|---|---|
| 5,234,781 A | 8/1993 | Sakamoto et al. | |
| 5,489,233 A | 2/1996 | Cook et al. | |
| 5,533,923 A | 7/1996 | Shamouilian et al. | |
| 5,562,530 A | 10/1996 | Runnels et al. | |
| 6,126,532 A | 10/2000 | Sevilla et al. | |
| 6,559,039 B2 | 5/2003 | Wang et al. | |
| 6,686,230 B2 | 2/2004 | Meiling et al. | |
| 6,958,277 B2 | 10/2005 | Pomarede et al. | |
| 7,459,914 B2 | 12/2008 | Lindsey et al. | |
| 2007/0039920 A1 | 2/2007 | Kutchoukov et al. | |
| 2007/0178655 A1 | 8/2007 | Schmidt et al. | |
| 2008/0180188 A1 | 7/2008 | Beerling et al. | |
| 2008/0242556 A1 | 10/2008 | Cao et al. | |
| 2009/0042373 A1 | 2/2009 | Zollner et al. | |
| 2009/0115094 A1 | 5/2009 | Chou et al. | |
| 2009/0136948 A1 | 5/2009 | Han et al. | |
| 2009/0155877 A1 | 6/2009 | Iliescu et al. | |

OTHER PUBLICATIONS

J. Haneveld, "Nanochannel Fabrication and Characterization Using Bond Micromachining", Ph.D. Thesis, University of Twente, Enschede, The Netherlands, ISBN 90-365-2312-5, 2006.*

Abstract—Pingshan Wang, "Broadband dielectric spectrometers with 1-10 nm planar nanofluidic channels", National Science Foundation, Jun. 30, 2009.

* cited by examiner

*Primary Examiner* — Lan Vinh
*Assistant Examiner* — Jiong-Ping Lu
(74) *Attorney, Agent, or Firm* — Dority & Manning, PA

(57) ABSTRACT

Disclosed is a method for fabricating nanofluidic channels having a height of from about 1 nm to about 10 nm. Generally, the method includes formation of doped silicon parallel strips in a silicon substrate, formation of a native oxide layer on the substrate, and etching of the native oxide layer at one of the strips to form a channel of a depth of between about 1 nm and about 10 nm. The method also includes bonding a second wafer to the surface, the second wafer including through etched windows to provide probe contacts to two of the parallel strips during use. These parallel strips provide high-frequency transmission lines in the device that can provide broadband dielectric spectroscopy measurement within the nanochannels.

7 Claims, 11 Drawing Sheets

| IMAGE STATISTIC: | | BOX STATISTIC: | |
|---|---|---|---|
| IMG. Z RANGE | 638.68 nm | Z RANGE | 41.012 nm |
| IMG. MEAN | 0.0001 nm | MEAN | 61.109 nm |
| IMG. RAW MEAN | 697.46 nm | RAW MEAN | 779.48 nm |
| IMG. RMS (eq) | 66.218 nm | rms (eq) | 2.215 nm |
| IMG. RA | 64.904 nm | MEAN ROUGHNESS (Ra) | 1.598 nm |
| IMG. RMAX | 619.19 nm | MAX HEIGHT (Rmax) | 41.121 nm |
| | | BOX X DIMENSION | 18.647 μm |
| | | BOX Y DIMENSION | 18.490 μm |

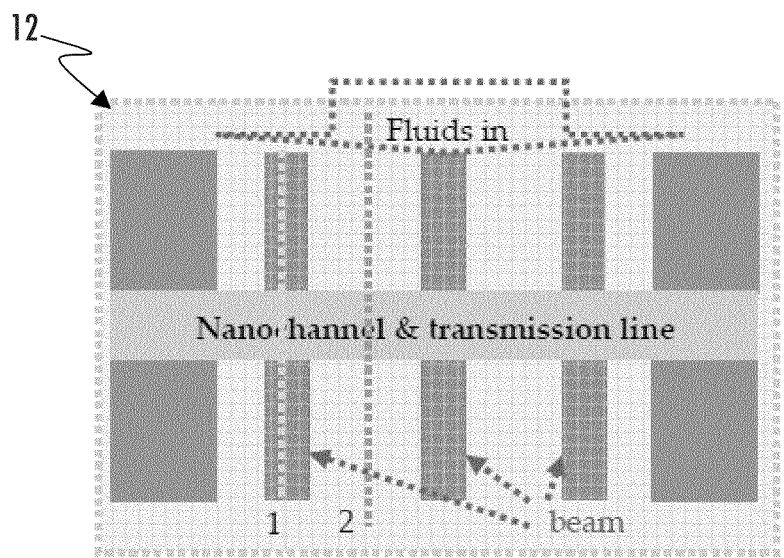
FIG. 8A
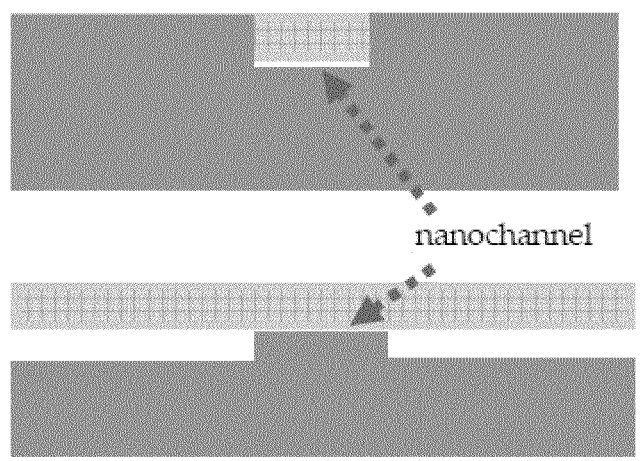
FIG. 8B
FIG. 8C

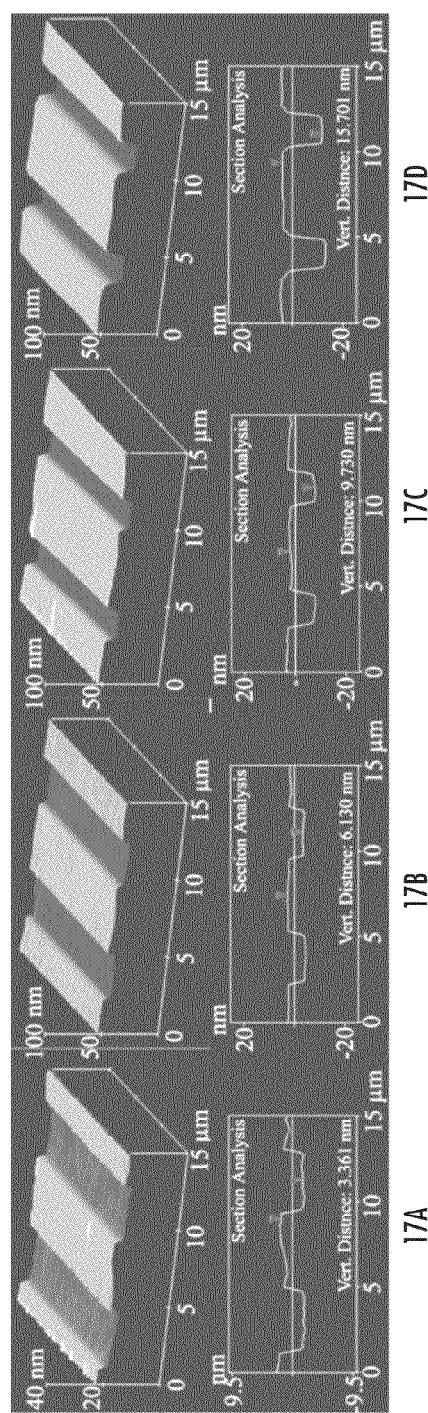
FIG. 17
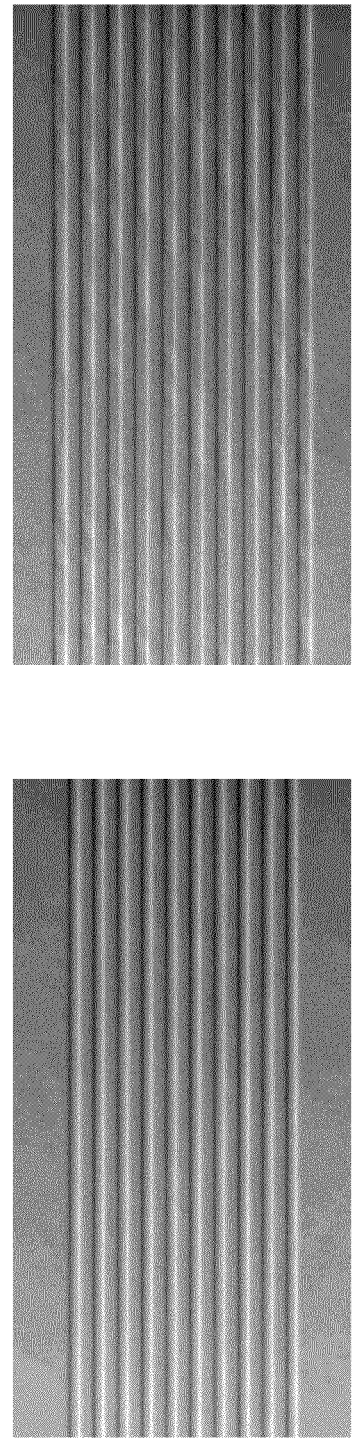
FIG. 18B
FIG. 18A

US 8,758,633 B1

DIELECTRIC SPECTROMETERS WITH PLANAR NANOFLUIDIC CHANNELS

CROSS REFERENCE TO RELATED APPLICATION

The present application claims filing benefit of U.S. Provisional Patent Application Ser. No. 61/229,127 having a filing date of Jul. 28, 2009 which is incorporated herein in its entirety by reference thereto.

STATEMENT REGARDING FEDERALLY SPONSORED RESEARCH OR DEVELOPMENT

This invention was made with government support under Grant No. 2095549/FA9550-06-1-0505 awarded by the United States Army/Army Research Office and under Award No. 0925424 awarded by the National Science Foundation. The government may have certain rights in the invention.

FIELD OF THE INVENTION

The present subject matter relates to fabrication of planar nanofluidic channels. More specifically, the present subject matter discloses methods for fabricating planar nanofluidic channels at heights of about 1 nm to about 10 nm.

BACKGROUND OF THE INVENTION

Planar nanofluidic channels are powerful tools for the investigating of materials under confinement such as confined water, DNA and proteins. The channels are also essential components in nanofluidic systems.

Some materials naturally include nanochannels or a random network of pores. For example, carbon nanotubes, zeolites and polymers such as poly(vinyl methyl ether) (PVME) and polyvinylpyrrolidone (PVP) have nanochannels. However, many limitations with utilizing nanochannels in these materials exists, such as their randomness, the difficulty of controlling and modifying their pore surfaces uniformly and consistently, the difficulty of studying the effects of external electric fields, and the occurrence of parasitic signals that obscure test readings.

Various methods such as wet-etch and dry-etch of silicon and silicon dioxide thin films have been developed for the fabrication of nanochannels from about 20 nm to 100 nm. For example, techniques developed from traditional semiconductor processing such as patterning, thin film deposition, etching and wafer bonding have produced nanochannels from about 20 nm to 100 nm, mainly for nanofluidic research and bio-molecule separation and detection investigations.

Unfortunately, difficulties in producing nanofluidic channels having a height of from about 1 nm to about 10 nm remain. Channels having a height from about 1 nm to about 10 nm would be useful for many scientific and engineering investigations, including confinement effect research, tribology studies and biology studies. For example, nanofluidic channels have been used with dielectric spectrometers to measure the effects of an electric field on a liquid or gas. Dielectric spectrometers probe the interactions between a time-dependent electric field and molecules that are polarized and/or charged. The ability to form nanofluidic channels of a smaller height could greatly improve such devices.

Dielectric spectrometers having nanofluidic channels can be used to detect and analyze biological molecules, cells, their dynamic processes and surface interactions, such as protein and DNA analysis (including DNA folding-unfolding process analysis), cell detection and analysis, molecular structure analysis, and bimolecular surface interactions; analyze the dynamics of glass-forming liquids (such as glycerol) and supercooled liquids (compared with other experimental instruments, dielectric spectroscopy is proving to be an ideal tool to study the relaxation processes of these materials); study the molecular dynamics of polymers; in-situ sensing and monitoring; and investigate molecular dynamics in confined spaces. Examples of confined liquids include biological water between two membranes and liquid lubricants between two friction surfaces. Since both are only a few molecules thick, dielectric spectroscopy with nanofluidic channels enables the study of the dynamic interactions between surfaces and confined liquids.

While various methods for fabricating planar nanofluidic channels have been developed, room for improvement in the art exists.

SUMMARY OF THE INVENTION

In view of the recognized features encountered in the prior art and addressed by the present subject matter, an improved method for fabricating nanofluidic channels has been developed.

According to one embodiment, a method for forming a planar nanofluidic channel on a substrate is disclosed. A method can include, for instance, growing a native oxide layer on a surface of a silicon substrate, the silicon substrate including a region of p-type or n-type doped silicon at the surface; etching the native oxide layer at the region of the p-type or n-type doped silicon according to a patterned wet oxide etch, the etching removing about 1 nm of material from the region; and bonding a second substrate to the surface of the silicon substrate, this second substrate being bonded to the lower substrate such that a portion of the second surface of the second substrate forms a top of the planar nanofluidic channel. For instance, the substrates can be bonded together according to an anodic bonding process.

In one embodiment, a method can also include forming the region of p-type or n-type doped silicon. In addition, transmission lines can be formed on either side of the region of p-type or n-type silicon. For instance, when the center region is p-type, the transmission lines can be n-type and vice versa.

The etching step can be repeated one or more times in order to obtain the desired depth of the nanofluidic channel. A native oxide layer can be grown over the etch area prior to each etching step.

Also disclosed are silicon substrates formed according to disclosed methods. The nanofluidic channel can have a height of between about 1 nm and about 10 nm as measured from the base of the channel to the top of the channel. A nanofluidic channel can have a width of between about 200 nm and about 1 μm and the base surface of the planar nanofluidic channel can have a surface roughness of between about 0.4 nm and about 0.6 nm.

Also disclosed are methods for measuring dielectric properties of a fluid in which an electric field can be induced across a device that defines a nanofluidic channel as described herein. A method can also include wetting the channel with the fluid and measuring one or more dielectric properties of the fluid.

In one embodiment, the fluid can be a liquid that contains a biological molecule such as a polypeptide or a polynucleotide. In one embodiment, the liquid can carry a cell.

BRIEF DESCRIPTION OF THE DRAWINGS

A full and enabling disclosure of the present invention, including the best mode thereof, directed to one of ordinary skill in the art, is set forth in the specification, which makes reference to the appended Figures, in which:

FIG. 8A illustrates an overhead view of beams on a lower substrate to provide mechanical support to one embodiment of disclosed devices. FIG. 8B illustrates a nanochannel of FIG. 8A along line 1 of FIG. 8A. FIG. 8C illustrates a cross section view of the nanochannel along line 2 of FIG. 8A.

FIG. 17 illustrates AFM images and section analysis of nanofluidic channels formed according to a method as described herein utilizing multiple HF etching dips including a 3 dip process (FIG. 17A), a 6 dip process (FIG. 17B), a 9 dip process (FIG. 17C), and a 15 dip process (FIG. 17D).

FIGS. 18A and 18B are microscopy images of 6 nm deep channels including 3 μm wide channels (FIG. 18A) and 4 μm wide channels (FIG. 18B). Each group contains 10 nanofluidic channels spaced 5 μm apart.

Figure 1:
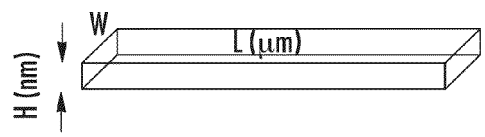
FIG. 1 is a schematic illustrating one embodiment of a planar nanofluidic channel as may be formed as disclosed herein.

Repeat use of reference characters throughout the present specification and appended drawings is intended to represent same or analogous features or elements of the invention.

DETAILED DESCRIPTION OF THE PREFERRED EMBODIMENTS

Reference will now be made in detail to the presently preferred embodiments of the subject fabrication methods, products produced from the fabrication methods, and methods of measurement using the fabricated products.

It is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the Figures or stated in the detailed description of such Figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

In an exemplary configuration, nanofluidic channels having a height of about 1 nm to about 10 nm may be produced. In one embodiment, a method can include forming parallel strips of doped silicon on a silicon substrate. For example, two strips for use as transmission lines can be developed including p-type doping and a strip therebetween for use as a nanofluidic test channel can be developed from an n-type doped silicon. Following, a native oxide layer is grown across the substrate. The oxide layer is then etched over the nanofluidic test strip via a patterned oxide wet etch. This process can then be repeated to form a nanofluidic channel of a desired height. Following, a second wafer is bonded to the lower wafer such that the gap formed between the upper surface of the exposed strip of the nanofluidic channel and the lower surface of the second wafer forms an enclosed nanofluidic channel. Finally, the second, upper silicon wafer can be etched via through wafer etching to form probe contact windows at the transmission strips to form transmission channels.

In accordance with aspects of still further embodiments of the present subject matter, a method for dielectric spectroscopy measurements using the nanofluidic channels can be obtained. The method generally includes attaching a power source to the transmission lines formed in a device including a nanofluidic channel to induce an electric field across the substrate. Calibration measurements are then made to determine the distortion effects from the doped silicon transmission lines. The nanofluidic channel is then wetted with a material of interest. Dielectric properties may then be measured.

Fabrication of 1-10 nm Planar Nanofluidic Channels with Broadband Transmission Lines.

According to one embodiment, disclosed is a method for fabricating a device including at least one planar nanofluidic channel and also including transmission lines as may be utilized for broadband transmission. In one preferred embodiment, the planar nanofluidic channel can be between about 1 and about 10 nm in height. The method generally includes developing parallel strips of doped silicon on a silicon substrate. For instance, two of the strips can be utilized as transmission lines, and can include a p-type dopant, and a center strip can be used in forming a nanofluidic testing channel, and can include an n-type dopant. Following formation of the parallel strips, chemical mechanical polishing can be carried out so as to form an atomically flat silicon surface. Following, an oxide layer can be grown over the substrate including the formed strips. Etching of the oxide layer at one of the strips can be carried out by use of a patterned oxide wet etch. The native etching process can be carried out multiple times to provide a channel with the desired height. A second wafer can be bonded to the surface of the formed structure, and through wafer etching can be carried out to open windows over the transmission lines for probe contact.

As used herein, the term "nanofluidic channels" generally refers to a channel having at least one critical dimension from about 1 nm to about 100 nm. For example, FIG. 1 illustrates a channel as may be formed according to disclosed methods. Targeted channel dimensions can include a width W of from about 200 nm to about 1 µm; a length L of from about 200 nm to about 250 µm; and a height h of from about 1 nm to about 10 mm. Aspect ratio of a nanofluidic channel can be as small as 0.001, for instance less than about 0.0005, or between about 0.001 to about 0.002. Of course, nanofluidic channels having larger aspect ratios are also encompassed herein.

Figure 2A:
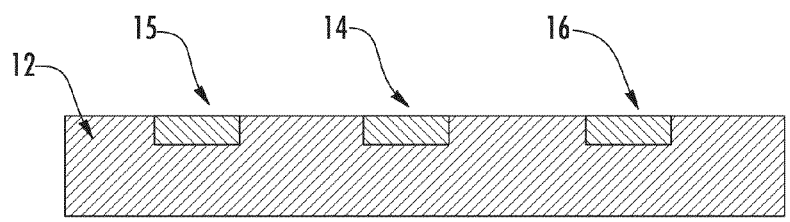
FIG. 2A is a front view of a first step in nanochannel fabrication in which parallel transmission lines and a nanofluidic channel line can be developed on a silicon wafer.

Referring to FIG. 2A, a substrate 12 is provided. For example, the substrate 12 may be a silicon wafer. The process can apply to any type of Si wafers with different doping levels. The substrate 12 may be slightly doped so as to provide the wafer with an essentially uniform initial doping. In an exemplary embodiment, the substrate 12 may be a p-type doped silicon wafer as is generally known in the art. In another embodiment, substrate 12 can be a bare N-type silicon wafer of 0.002-0.005 Ω·cm resistivity.

Initially, parallel strips 14, 15, 16 may be developed on a substrate 12. For instance, strips 14, 15, 16 can be developed to include n-type and p-type dopants to define an inner strip 14 and two outer strips 15, 16 of doped silicon materials. For example, inner strip 14 may be developed of n-type doped silicone, including any of the Group V dopants, e.g., N, P, etc. and the outer strips 15, 16 may be developed of p-type doped materials including any of the Group III dopants, e.g., B, Al, Ga, etc.

The parallel strips can be formed according to any suitable process. For instance, in one embodiment, strips 14, 15, 16 can be formed according to a patterned mask process. Patterned mask lithography techniques are well known in the art. By way of example, patterned mask etching and deposition processes as described in U.S. Pat. Nos. 5,234,781, 6,559,039, 6,686,230, and 6,958,277, all of which are incorporated herein by reference thereto, can be utilized in forming parallel channels of doped silicon materials on the disclosed devices. In general, a patterned mask technique involves removal of a portion of the silicon substrate surface at a specific location, and deposition of a doped silicon material at that location to form a strip of the doped silicon material at the substrate surface.

Figure 7:
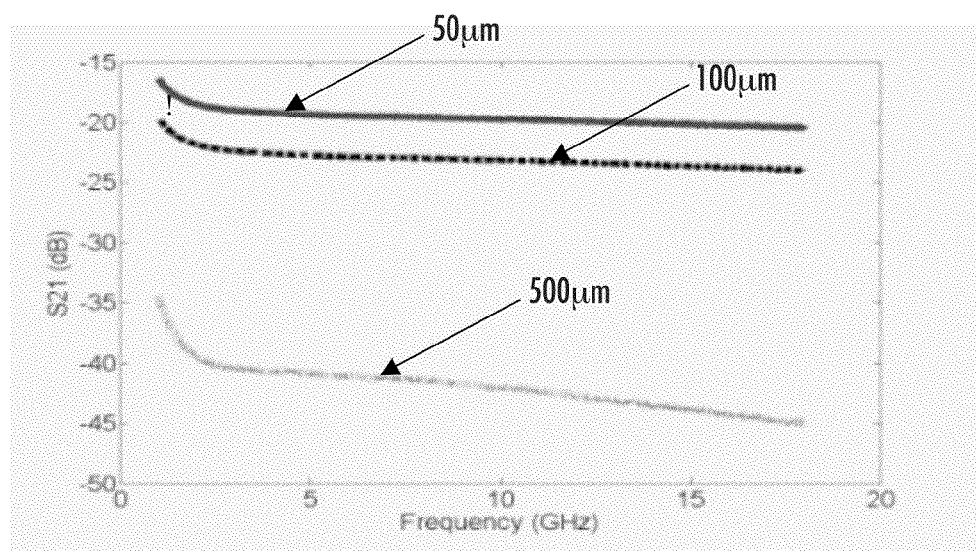
FIG. 7 shows signal transmission coefficients for doped silicon transmission lines of disclosed structures of different lengths.

According to the embodiment illustrated in FIG. 2A, the outer strips 15, 16 can define transmission lines of the final device. The outer strips 15, 16 can beneficially be formed of a material so as to enable broadband characterization capabilities. For instance, FIG. 7 illustrates signal transmission coefficients of doped silicon microstrip transmission lines with different lengths. As illustrated, the line loss is reasonable as long as the line length is not too long, for example below about 500 µm. Line loss can increase when fluids are included with the transmission lines, for instance, a 1 mm long device formed as described herein has an approximate 20 dB loss increase upon inclusion of water in the channel. However, these silicon based transmission lines can provide suitable performance of broadband dielectric spectroscopy studies over the distances proposed.

Figure 3A:
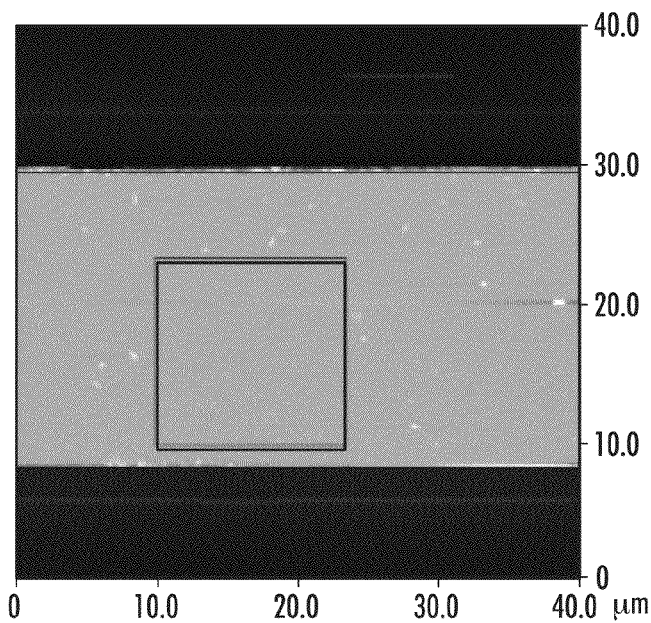
FIG. 3A is an AFM image of a gold transmission line showing average surface roughness.
Figure 3B:
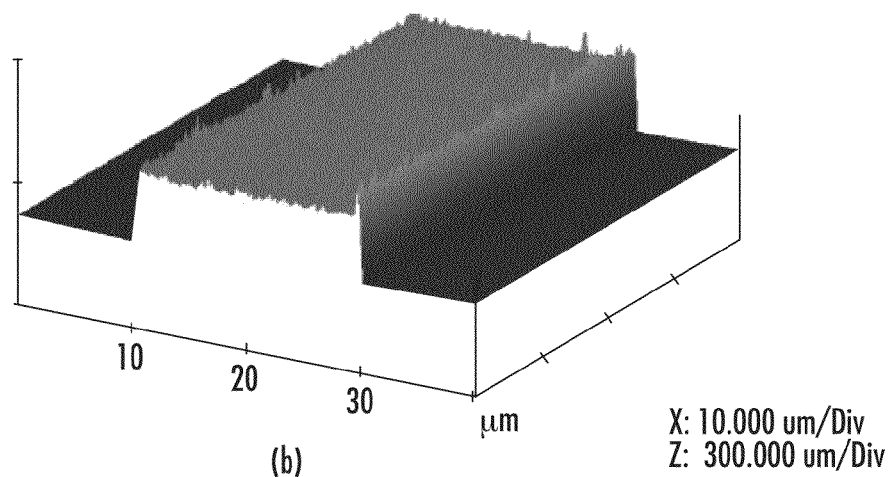
FIG. 3B is a 3-D rendition of the AFM image in FIG. 3A.

Through utilization of doped silicon to form the transmission lines rather than traditional metal thin films, electrode surface roughness and flatness can be improved. For example, as illustrated in FIGS. 3A and 3B, a gold metal transmission line was examined using atomic force microscopy (AFM). As shown, the average surface roughness was 2.2 nm, which is too great for achieving a nanofluidic channel height as sought herein.

The inner strip 14 can include a suitable dopant so as to encourage the desired electrical fields across the device following formation. For instance, strip 14 can be formed of an n-type doped material parallel to and between transmission strips 15, 16. Strip 14 can be formed according to the same or a different method as strips 15, 16. For instance, in one embodiment, strip 14 can be formed according to a patterned mask etching and deposition process, as is generally known in the art.

Strips 14, 15, 16 can be formed to a depth so as to ensure adequate contact and development of desired electrical fields.

Following formation, the silicon substrate 12 including strips 14, 15, 16 may be chemically and mechanically polished so as to obtain a substantially atomically smooth surface by methods known to those of ordinary skill in the art. For example, chemical mechanical polishing (CMP) methods as disclosed in any of U.S. Pat. Nos. 5,489,233, 5,533,923, 5,562,530, 6,126,532, or 7,549,914, all of which are incorporated herein by reference can be utilized to polish the surface of the substrate to an atomic level surface smoothness. Advantageously, CMP processes can obtain the desired level of smoothness in disclosed substrates as there need not be any heterogeneous materials (e.g., metal strips) in the substrates to cause dishing or other problems.

Figure 2B:
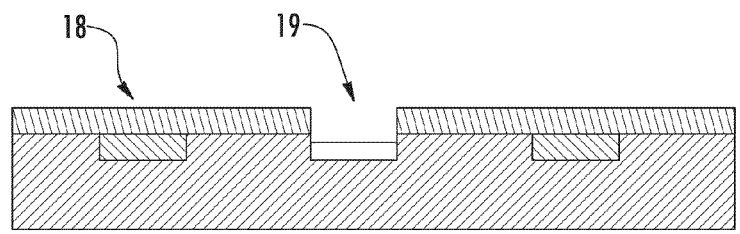
FIG. 2B is a front view of a second step in nanofluidic channel fabrication in which a native oxide layer can be grown over the surface of a wafer including doped lines.

Referring now to FIG. 2B, a layer of native oxide 18 may be grown across the silicon substrate 12 following formation of the strips 14, 15, 16 at the surface of the substrate 12. As is known in the art, a thin layer of silicon dioxide (i.e., native oxide) of about 1 to 2 nm is formed on a silicon surface when the silicon surface is exposed to oxygen.

As also shown in FIG. 2B, the native oxide growth atop the strip 14 as well as a portion of strip 14 can be removed during a patterned wet oxide etch leaving a channel 19 in the substrate surface. The surface can be patterned according to standard photoresist methodology. For instance, MICROPOSIT™ photoresist S118 with a thickness of less than about 1.8 µm can be used to pattern the channels through standard photolithography procedures.

In one preferred embodiment, patterned wet hydrofluoric acid (HF) etching with diluted (e.g., about 100:1 HF) may be used to remove the native oxide growth over the strip 14 and a portion of the material forming strip 14. The photoresist serves as mask material during HF dip etch. The method and materials utilized to remove the materials to form channel 19 is not limited in any particular way. For example, in another embodiment, a TetraMethyl Ammonium Hydroxide (TMAH) etch may be used to remove native oxide growth and a portion of the doped silicon at strip 14 to form channel 19.

The etch step can be repeated to obtain the desired channel depth of the final nanofluidic channel. For instance, it has been found that each etch dip utilizing an HF dip process can increase the channel depth by about 1 nm through removal of the native oxide layer followed by removal of a portion of the doped silicon material forming strip 14. Thus, multiple etch steps may be used to achieve different desired channel depths. In one embodiment, native oxide can regrow at the etched area under ambient conditions for a period of time (e.g., about one day) between individual etching steps. The wait time between successive dips is not critical and can be reduced as desired, for instance if throughput is a concern. For example, a 1-2 h wait time can be sufficient to grow 0.6 nm thick oxide based on the characteristics of native oxide growth in an ambient environment.

The etch, regrow, etch process can then be repeated until the desired trench depth is achieved. As 44% of the native oxide layer thickness will be from the Si substrate, the obtained trench depth can be 0.44nT, where n is the number of etching dips and T is the thickness of the native oxide that can be easily and accurately obtained in a temperature and humidity controlled environment, e.g., in a cleanroom. At the end of trench etch, the photoresist mask can be removed by soaking into heated solvent 1165 (e.g., about 70° C.).

Figure 4:
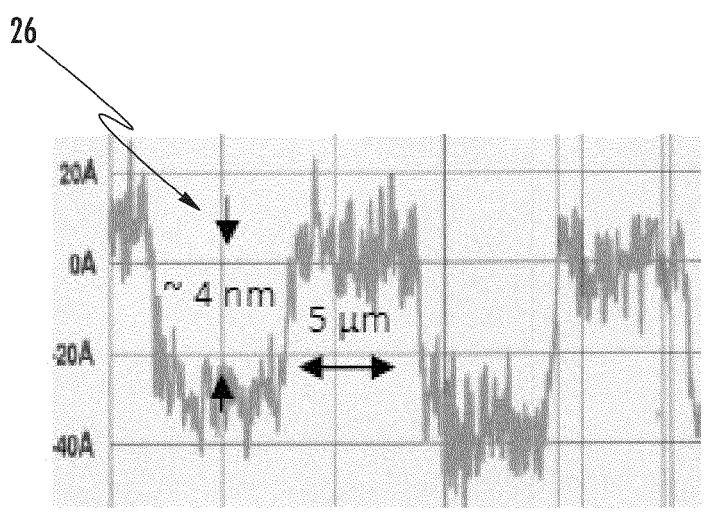
FIG. 4 is an image of depth profile measured by use of P10 Profilometer, illustrating formation of an approximately 4 nm nanofluidic channel formed into a silicon substrate.

The surface roughness of the channels does not deteriorate when deeper channels are formed with multiple etch dips. For example, FIG. 4 illustrates a device formed as described herein including a nanofluidic channel 26 of about 4 nm. In one embodiment, rms surface roughness can be between about 0.4 nm and about 0.6 nm.

Good etch uniformity can be achieved across a wafer as etch time is not critical due to extremely high HF selectivity between Si and $SiO_2$. High selectivity implies very low Si etch rate even when defects are present in an Si substrate. Therefore, the multidip process can be utilized and provide excellent results even when considering a Si substrate that includes defects.

Figure 2C:
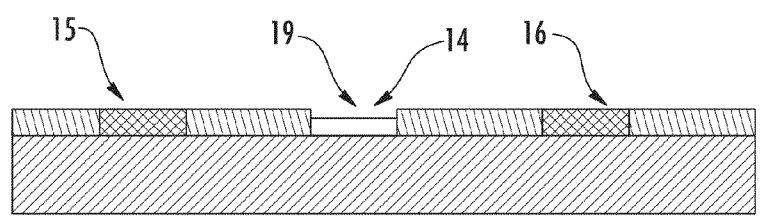
FIG. 2C is a front view of a third step in nanofluidic channel fabrication in which a native oxide layer can be removed via a patterned oxide wet etch over one of the doped lines.

Following multiple etching steps to form a desired channel height at 19, the remaining native oxide growth on the substrate 12 may be removed by etching as illustrated in FIG. 2C. For example, the native oxide 18 growth may be removed by wet HF etching.

Figure 2D:
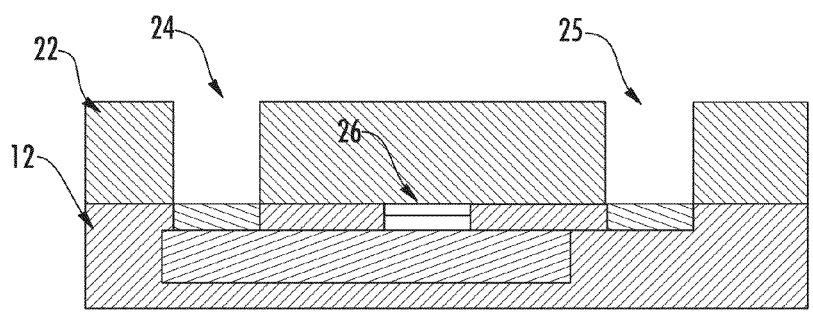
FIG. 2D is a front view of a fourth step in nanofluidic channel fabrication illustrating the wafer of FIG. 2C bonded to a second etched silicon wafer.

Referring now to FIG. 2D, a second substrate 22 may be bonded to the surface of substrate 12. Prior to the bonding of substrate 12 and second substrate 22 windows 24, 25 may be opened in second substrate 22 to provide probe contacts in the final device. The probe contact windows 24, 25 may be formed by any method known to those of ordinary skill in the art. For example, the probe contact windows 24, 25 may be formed by through etching of a second substrate 22.

Second substrate 22 can be formed of the same or different material as substrate 12. For instance, in one preferred embodiment, second substrate 22 and substrate 12 can both be p-type silicon wafers as are known in the art. In another embodiment, second substrate 22 can differ, however. For instance, substrate 12 can be formed of a p-type silicon, and second substrate 22 can be glass, quartz, and so forth.

Multiple wafer bonding methods are known in the art, any of which may be utilized in disclosed methods. In general, preferred wafer bonding methods can depend upon the specific materials utilized in substrate 12 and second substrate 22. For instance, silicon direct bonding techniques, anodic bonding techniques, and so forth can be utilized. In one preferred embodiment, a low-temperature (e.g., less than about 225° C.), low-voltage (e.g., less than about 400 V) anodic wafer bonding process can be utilized.

The second substrate 22 including probe contact windows 24, 25 may be bonded to the substrate 12 to form a nanofluidic channel 26 having a height from about 1 nm to about 10 nm. The probe contact windows 24, 25 allow for a voltage source to be connected to the transmission lines 15, 16 enabling an electric field to be applied uniformly across the device.

Because the silicon substrate surfaces remain unaffected during the etching of the nanofluidic channel, improved wafer bonding with the second substrate 22 including probe contact windows 24, 25 may be obtained.

The nanofluidic channel may then be wetted to confirm that the nanofluidic channel has not collapsed, nor leaked. According to one embodiment, disclosed structures can include the addition of a combination of additional support beams, illustrated in FIG. 8. Additional support beams can prevent collapse of the nanochannels both during the fabrication process as well as during use. FIG. 8A illustrates an overhead view of beams on a substrate 12 to provide mechanical support to disclosed devices. FIG. 8B illustrates a nanochannel of FIG. 8A along line 1 of FIG. 8A. FIG. 8C illustrates a cross section view of the nanochannel along line 2 of FIG. 8A.

According to another embodiment, potential collapse of the nanochannels can be prevented through control of channel aspect ratio, e.g., L vs. H of FIG. 1.

Figure 9A:
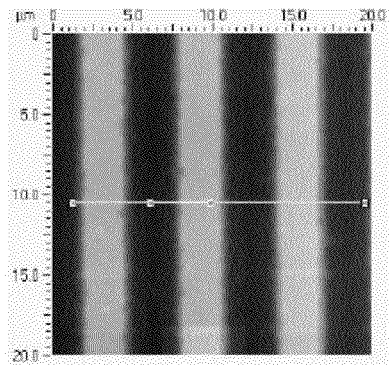
FIGS. 9A and 9B are an atomic force micrograph (AFM) and 3D image of an array of nanochannels formed as described herein.
Figure 9B:
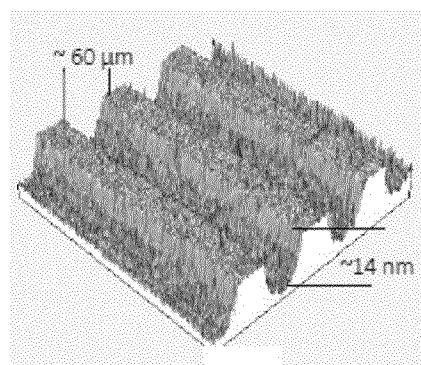
Figure 10:
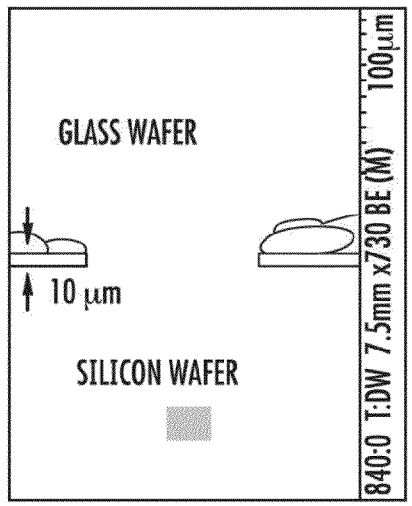
FIG. 10 is a device formed as described herein.
Figure 11:
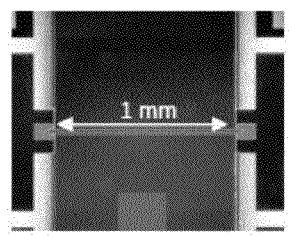
FIG. 11 is another device formed as described herein.

Exemplary structures formed according to disclosed methods are illustrated in FIGS. 9, and 11. Specifically, FIG. 9A is an AFM picture of array including a series of approximately 14 nm deep nanochannels. FIG. 9B is a 3D image of the array in FIG. 9A. FIG. 10 is a scanning electron micrograph (SEM) of a glass and a silicon wafer bonded via an anodic wafer bonding method to form an array of 10 μm nanochannels within the structure. FIG. 11 illustrates a bonded microfluidic channel having a 1 mm width and a nanometer height.

Broadband Dielectric Spectroscopy Methods Using the Developed Substrate Having a Nanofluidic Channel.

Also disclosed herein is a method for measuring dielectric properties of a material within a nanofluidic channel formed as described above. With reference to FIG. 2, discussed above, the method generally includes attaching a power source to the transmission lines 15, 16 to induce an electric field across a device. Calibration measurements can then be made to determine the distortion effects from the doped silicon transmission lines. The nanofluidic channel 26 can then be wetted with a material of interest. Dielectric properties may then be measured within the channel.

Beneficially, disclosed devices include high frequency transmission lines that can provide broadband dielectric spectroscopy measurement within the nanochannels. In one embodiment, the frequency range of disclosed devices can be from about 3 kHz to about 50 GHz, similar to frequency range of existing network analyzers.

Figure 5:
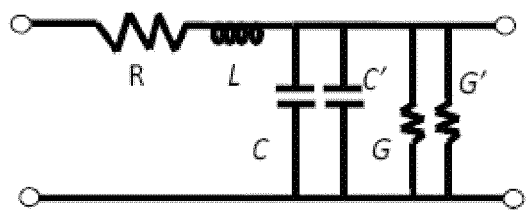
FIG. 5 is an RLCG equivalent circuit diagram of an on-chip microstrip line with water.

For example, the measurement method may be based on the equivalent transmission line model as illustrated in FIG. 5. As illustrated, C' and G' represent the effects of the material under test (MUT) dielectric property, which is defined by the equation:

$$\in_x(\omega) = \in_x' - j\in_x''$$

The obtained permittivity is related to MUT relaxation constant, τ. For instance, if Debye-type dispersion is assumed, the relationship becomes:

$$\varepsilon_x(\omega) = \varepsilon'_x - j\varepsilon''_x = \frac{\varepsilon_s - \varepsilon_\infty}{1 - i\omega\tau}$$

where $\in_s$ and $\in_\infty$ refer to MUT permittivity at DC and infinite frequency, respectively. As described, broadband measurements, defining relaxation time constant, τ, are possible utilizing devices formed as described herein.

The MUT dielectric properties under different DC electric fields may be obtained by simultaneously applying a DC voltage across the broadband transmission lines. Possible DC voltage pull-in issues may be mitigated, for example, by using supporting beams on the bottom wafer. As previously discussed, the supporting beams may prevent the wafer from collapsing during wafer bonding, for instance during anodic bonding methods when forming glass-silicon wafer combinations.

Figure 6:
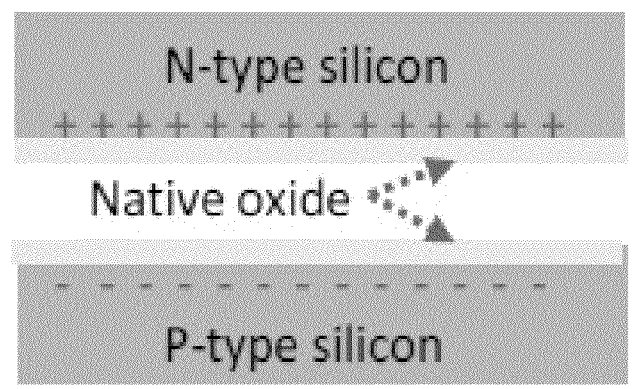
FIG. 6 shows the formation of depletion regions when a channel is reversed biased.

As illustrated in FIG. 6, the application of DC electric fields may induce depletion regions when the channel is "reversed biased." However, the depth of the depletion regions may be controlled by control of the doping of the transmission lines. The occurrence of the depletion regions can be very similar to the charge layers in a metal-oxide-semiconductor (MOS) field effect transistor.

Since transmission lines are formed by doped silicon, which has frequency and electric field intensity dependent properties, detailed characterizations and calibration can be performed to minimize the adverse effects of silicon substrates. Such characterizations and calibrations are well within the capabilities of one of ordinary skill in the art and thus, are not discussed at length herein.

Dielectric spectrometer measurement methods as described herein can be useful in detecting and analyzing biological molecules, cells, their dynamic process and surface interactions. Biological molecules can include, without limitation, polypeptides, e.g., entire proteins, protein fragments, oligopeptides, and so forth; polynucleotides including natural and synthetic RNA and DNA; polysaccharides; and so forth. Disclosed methods can include DNA analysis (including DNA folding-unfolding process analysis), cell detection and analysis, molecular structure analysis, and biomolecular surface interactions.

The present disclosure may be better understood with reference to the Examples, provided below.

Example 1

A process as described herein was utilized to form nanofluidic channel on an N-type silicon wafer. A multiple HF-dip etch process was carried out utilizing dilute HF solution (100:1). Following an etch process, native oxide was allowed to regrow at the etched area under ambient conditions for a period of one day. MICROPOSIT™ S1818™ positive photoresist with a thickness of ~1.8 μm was used to pattern the trenches. Following the desired number of iterations, the photoresist mask was removed by soaking in heated MICROPOSIT® REMOVER 1165.

Figure 12:
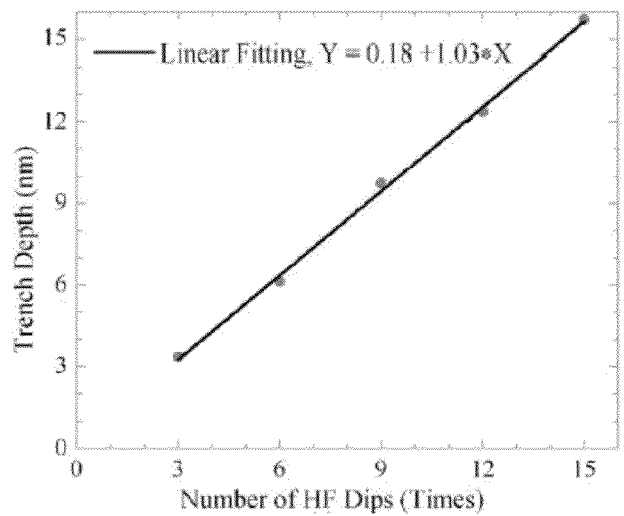
FIG. 12 graphically illustrates the trench depth vs. the number of HF etch dips utilized in a formation process as described herein.
Figure 13A:
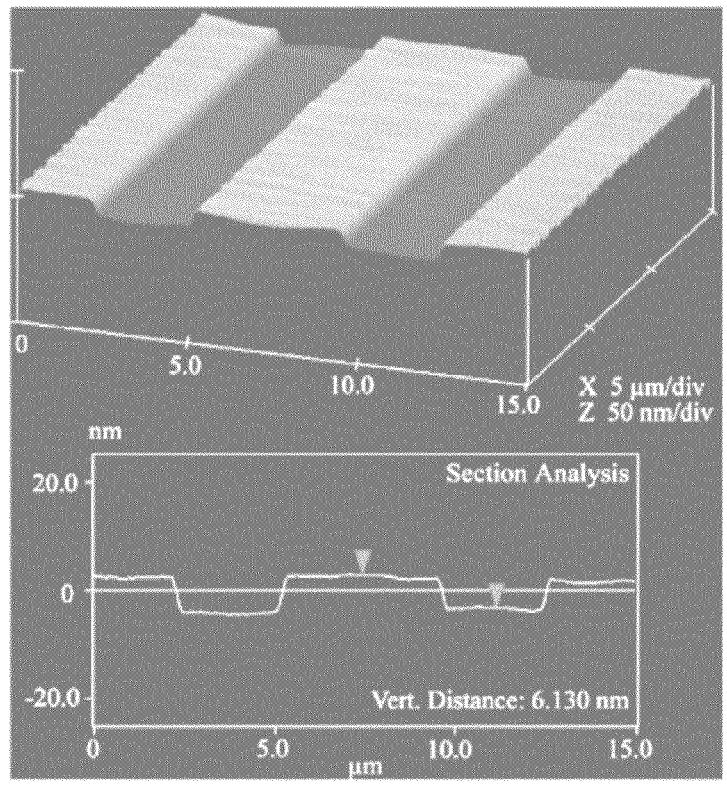
FIG. 13A illustrates an AFM 3-D view and section analysis of a 6 nm deep Si trench formed according to disclosed methods.
Figure 13B:
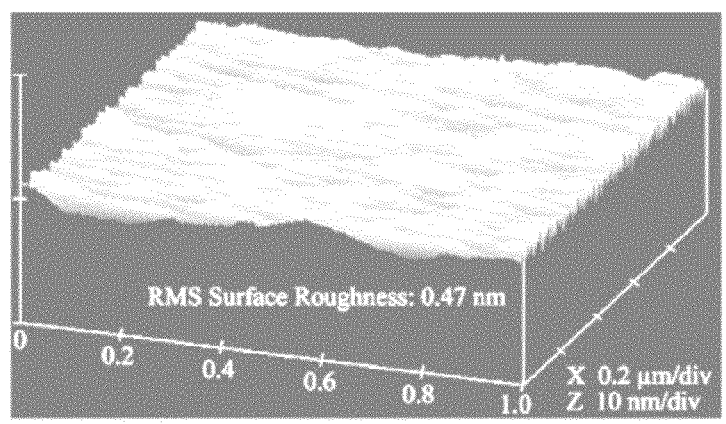
FIG. 13B illustrates the RMS surface roughness of 0.47 nm of a 6 nm deep Si trench obtained with AFM over a 1 μm×1 μm area.

FIG. 12 shows the obtained trench depths measured with atomic force microscopy (AFM) for different number of HF dips. As can be seen, well controlled shallow Si trenches can be obtained at an etch rate of less 1 nm/HF-dip. Thus, a trench of less than 1 nm is readily obtained by one HF dip. FIG. 13A shows an AFM 3-D view of a 6 nm deep Si trench and its section analysis. FIG. 13B shows an AFM rms surface roughness analysis over a 1 μm×1 μm area of the etched surface. As can be seen, very smooth etched surfaces are obtained with rms roughness of 0.4-0.6 nm for all etched trenches. The roughness is comparable to polished bare Si surface. Thus, the etched surface does not deteriorate after many HF dips, which also indicates that the etch process is insensitive to substrate defects. Therefore, the process preserves trench surface smoothness, which is critical for nanofluidics studies, especially for sub-10 nm channels.

Additionally, the surfaces that were protected by photoresist were intact, and the etch process is at room temperature and stress free, which did not cause wafer deformation. These conditions are beneficial for wafer bonding.

A 500 μm thick, 100 mm diameter Pyrex 7740 (borosilicate glass) wafer with 15° A or less surface roughness (Ra) and better than 10 μm flatness was used as the top wafer for channel formation.

Inlet/outlet access holes were mechanically drilled through the glass wafer for channels access. The temperature and voltage of anodic bonding is very process specific because it is affected by electrical and mechanical properties of both Si and Pyrex wafers, as is known in the art. Both wafers were thoroughly cleaned and their surfaces were treated to be hydrophilic prior to anodic wafer bonding, which was performed at a temperature of 225° C. and a voltage of −400 V. Tool force of 660 N was applied to counteract any wafer bowing and ensure the wafers were in uniform contact. The bonding process was terminated when 10% of the initial current was reached. After bonding, no voids were observed. When a sharp blade was inserted at the edges, the wafers were not separated and the edges were chipped, which indicated good bonding strength.

The low bonding temperature made glass deformation unlikely to occur, and the displacement resulting from electrostatic force during bonding was negligible since a thick glass wafer was used. In addition, channel widths (<20 μm) were relatively small compared with glass wafer diameters. As a result, possible channel height nonuniformity due to possible glass wafer bowing was negligible.

Figure 14A:
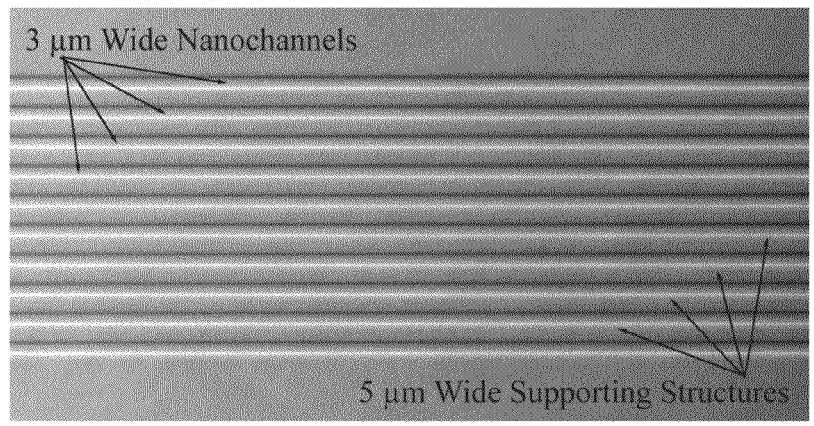
FIGS. 14A-14C are grayscale microscopy images (DIC mode) of 6 nm deep, 3 mm wide channels with 5 mm spaces (FIG. 14A); 6 nm deep, 4-μm wide channels with 5 μm spaces (FIG. 14B); and 15 nm deep channels (FIG. 14C). The channel widths of the channels of FIG. 14C are 15 μm, 20 μm, and 25 μm, respectively.
Figure 14B:
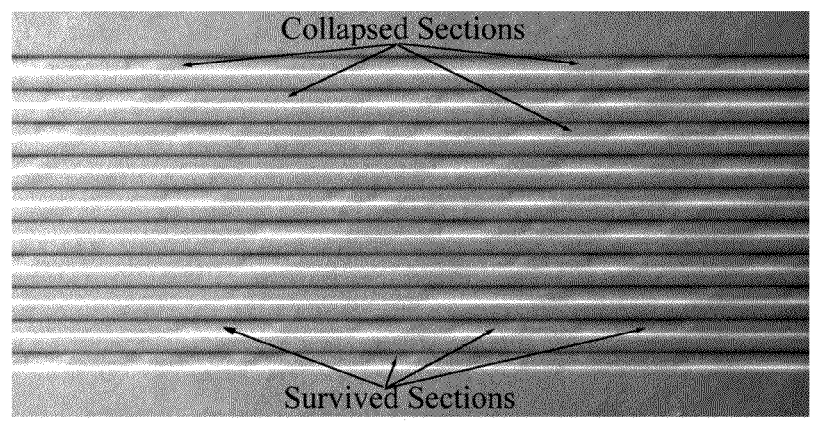
Figure 14C:
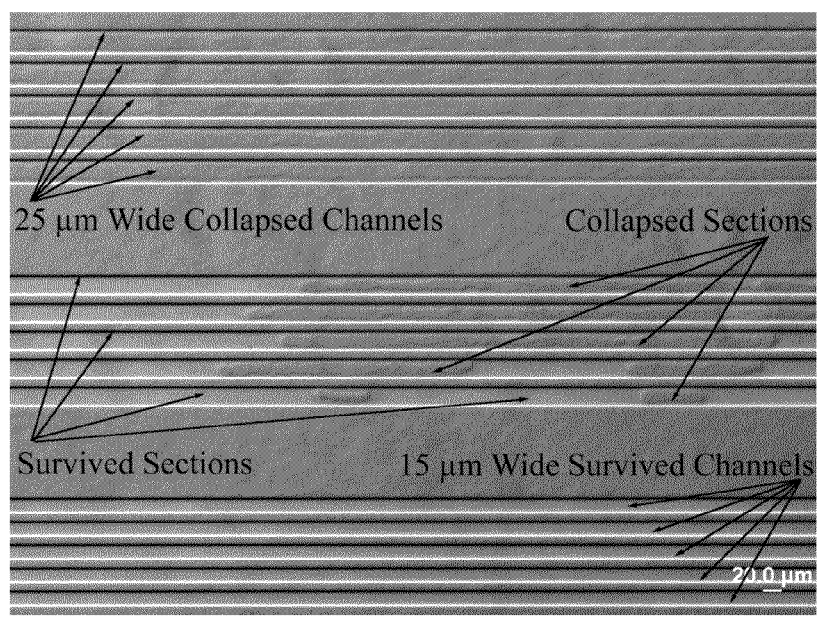

It is difficult to observe liquid flowing through a sub-10 nm nanofluidic channel due to its low contrast. Therefore, water-filling test could not be used to visually determine whether the sub-10 nm channel was collapsed or not. Instead, optical inspection was used to determine channel collapse or survival after wafer bonding. FIGS. 14A and 14B show microscopy images under differential interference contrast (DIC) mode for bonded 6 nm deep channels with a width of 3 and 4 nm, respectively. The images are converted to grayscale and the contrast is slightly adjusted to show the difference. The even tone inside the 3 μm wide channels indicates that the channels survived the bonding. The uneven tone inside the 4-μm wide channels indicates the collapse of the channels. When the depth of the channels increases, the contrast between the collapsed and survived channels increases. The observation method for channel collapse/survival is further applied to 15 nm deep channels. FIG. 14C clearly shows that 15 nm deep channels with a width of 15 μm survived, the 20 μm ones partially collapsed and the 25 μm ones totally collapsed.

Figure 15:
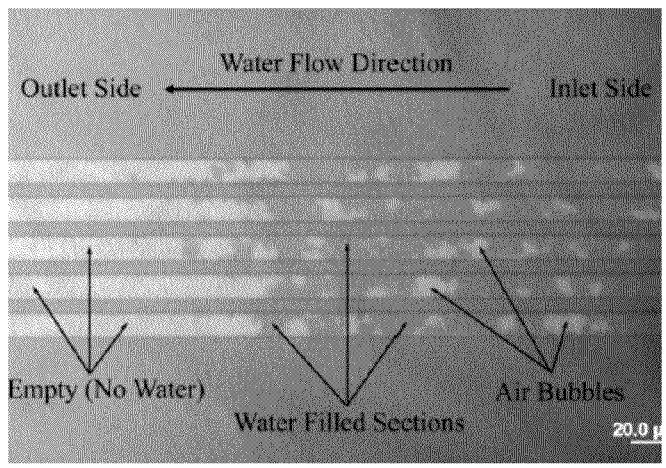
FIG. 15 is a still microscopy image (BF mode) of DI water flowing through 15 nm deep, 15 μm wide, and 15 mm long channels.

Water-filling (through capillary force) tests were conducted with the 15 nm deep and 15 μm wide channels to verify the optical inspection results. Deionized (DI) water was introduced into the inlet hole and flowed through the 15 mm long nanochannels. FIG. 15 shows a still microscopy image of the filling process under bright field (BF) mode. The image was taken at a position that was close to the outlet side, and it can be observed that the 15 µm wide channels are fully filled with DI water eventually, but no water is observed in 20 or 25 µm wide channels. The water filling observations agree with optical inspections under DIC mode.

SEM images of 10 nm planar channels formed via Si—Si fusion bonding were obtained (not shown). These channels were also fabricated by use of the disclosed multiple-dip trench formation techniques. The results showed that the channel was uniform with a height equal to the trench height before wafer bonding, similar to the Si-Pyrex channels. Furthermore, possible wafer bowing effects on channel height and uniformity could be neglected since the channels were narrow. Wafer deformation during bonding (due to temperature and voltage pulling) could also be ignored. Therefore, the obtained Si-Pyrex channel height was found to equal to the Si-trench depth, and the control of trench depth can transfer to control over channel height.

Table I summarizes the results of channel survival (Y) or collapse (N) for various depths and widths by optical inspection. The obtained minimum aspect ratios were 0.001-0.002, which are significantly lower than those channels that were previously reported with anodic wafer bonding techniques. The low voltage and low temperature formation methods are significant in achieving disclosed nanochannels with low aspect ratios.

TABLE 1

| Channel Depth (nm) | Channel Width (µm) | | | | | | | | | | | Minimum Aspect Ratio (depth/width) |
|---|---|---|---|---|---|---|---|---|---|---|---|---|
| | 2 | 3 | 4 | 5 | 6 | 7 | 8 | 9 | 10 | 15 | 20 | |
| 6 | Y | Y | N | N | N | N | N | N | N | N | N | 0.0020 |
| 9 | Y | Y | Y | N | N | N | N | N | N | N | N | 0.0022 |
| 12 | Y | Y | Y | Y | Y | Y | Y | Y | Y | N | N | 0.0012 |
| 15 | Y | Y | Y | Y | Y | Y | Y | Y | Y | Y | N | 0.0010 |

Compared with other nanochannel fabrication approaches, the aforementioned results illustrate that the disclosed approach is simple, easy to control and low-cost for sub-10 nm planar Si-channel fabrications.

Example 2

Figure 16:
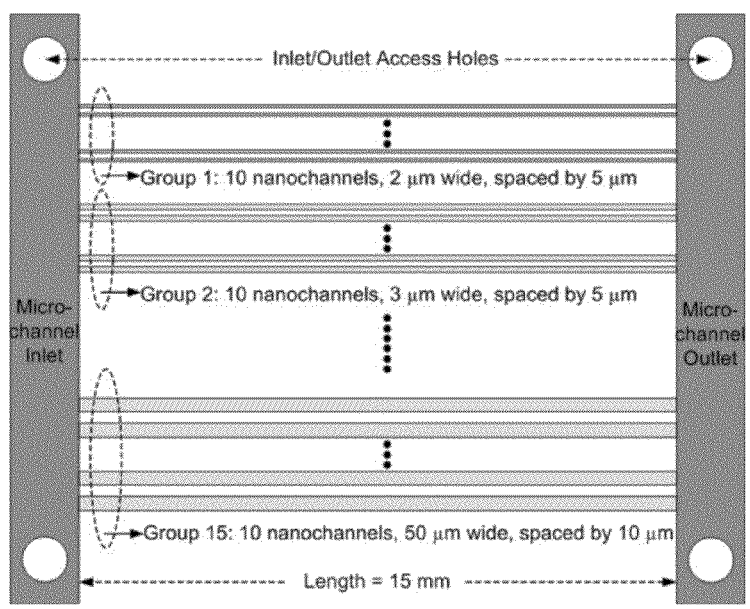
FIG. 16 is a schematic diagram of a layout design for a series of nanofluidic channels formed as described herein.

FIG. 16 illustrates the layout consideration of a series of nanochannels. A total of 10 parallel nanochannels were included in each group. Channels were 15 nm long with different channel width varying from 2 µm to 50 µm. Inlet and outlet are included for fluidic filling test. All fabrications were conducted in a class 100 cleanroom.

Methods as described above in Example 1 were used. N type 500 µm thick Si wafers with resistivity of 0.002-0.005 Ω·cm were exposed to air in a class 100 cleanroom environment with 22° C. average temperature and 44% RH average humidity. Standard photolithography steps were used for pattern transfer. Native $SiO_2$ was removed by dipping the wafer into 1% HF for 1 min. Native $SiO_2$ was allowed to re-grow for one day, followed by another HF dip. The HF dip and $SiO_2$ re-grow process steps were repeated until desired trench depth was obtained.

FIG. 17A-17D shows Atomic Force Microscopy (AFM) images of trenches obtained with 3, 6, 9 and 15 HF dips, respectively. The obtained depths were 3.3 nm, 6.1 nm, 9.7 nm and 15.7 nm, respectively. As shown, the multiple-HF-dip process yielded consistent etch rates (~1 nm/HF dip). Similar etch rates were obtained with different types of Si wafers and different resistivity. Therefore, the process had a good control of etch rates and trench depth. No start-up delay issues were observed.

Pyrex 7740 borosilicate glass wafer with thickness of 500 µm was used as top cover wafer. Its surface roughness Ra is less than 15 Å and its flatness is better than 10 µm. Inlet/outlet fluidic access holes were obtained through abrasive water jet cutter, which were eventually aligned to the nanofluidic channels on the bottom Si wafers. Both Si wafer and Pyrex 7740 were cleaned with RCA1 and RCA2 for 10 min, respectively. Following, the two wafers were quickly bonded as described above in Example 2.

Table 2 summarizes the results of channel survival (Y) or collapse (N) for different channel depths and widths. Microscopy inspections under Differential Interference Contrast (DIC) mode were used to evaluate channel integrities. Microscopy images under DIC mode as shown in FIGS. 18A and 18B illustrate that the 6 nm deep and 3 µm wide channels survived, yet 4 µm wide channels collapsed (blocked) at different places. The contrast differences inside the channels (FIG. 18B) indicate the collapse.

TABLE 2

| Channel Depth (nm) | Channel Width (µm) | | | | | | | | | | | | | | Min. Aspect Ratio (depth/width) |
|---|---|---|---|---|---|---|---|---|---|---|---|---|---|---|---|
| | 2 | 3 | 4 | 5 | 6 | 7 | 8 | 9 | 10 | 15 | 20 | 25 | 30 | 40 | 50 | |
| 6 | Y | Y | N | N | N | N | N | N | N | N | N | N | N | N | N | 0.0020 |
| 9 | Y | Y | Y | N | N | N | N | N | N | N | N | N | N | N | N | 0.0022 |
| 12 | Y | Y | Y | Y | Y | Y | Y | Y | Y | N | N | N | N | N | N | 0.0012 |
| 15 | Y | Y | Y | Y | Y | Y | Y | Y | Y | Y | N | N | N | N | N | 0.0010 |
| 24 | Y | Y | Y | Y | Y | Y | Y | Y | Y | Y | Y | Y | Y | Y | N | 0.0006 |

Figure 19A:
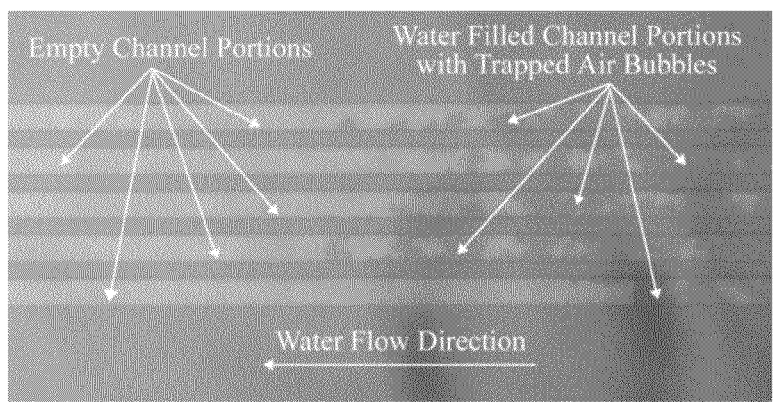
FIG. 19 illustrates channels during filling with water (FIG. 19A) and a fluorescence image following filling with high concentrated FITC dye in buffer solution (FIG. 19B).
Figure 19B:
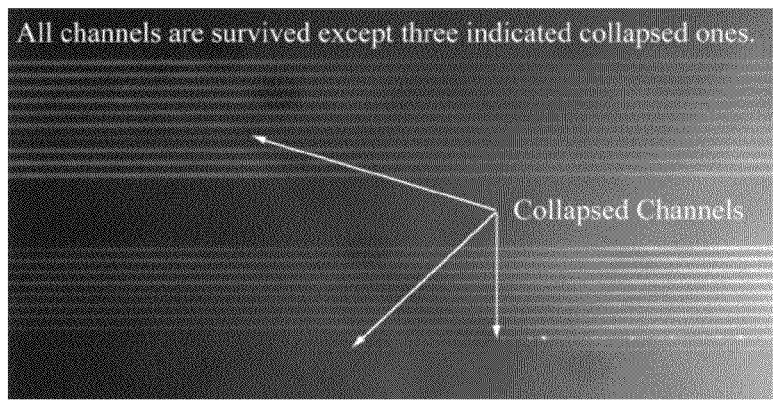

Fluidic filling tests were conducted to check channel formation. FIG. 19A shows a still image of water filling process for 15 nm deep and 15 µm wide channels. Air bubbles are observed during water movement due to very shallow channels. FIG. 19B shows a fluorescence image of 24 nm deep channels, which were filled with high concentrated FITC dye in buffer solution. It shows that most of the channels have survived except the three indicated collapsed.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art. Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

What is claimed is:

1. A method for forming a planar nanofluidic channel on a substrate comprising:
    growing a native oxide layer on a surface of a silicon substrate, the silicon substrate including a region of p-type or n-type doped silicon at the surface;
    etching the native oxide layer at the region of the p-type or n-type doped silicon according to a patterned wet oxide etch, the etching removing about 1 nm of material from the region
    forming second and third regions of doped silicon on the surface, the second and third regions being on either side of the region of p-type or n-type doped silicon, wherein the second and third regions are transmission lines; and
    bonding a second substrate to the surface of the silicon substrate, the second substrate comprising a first surface and a second surface, the second surface of the second substrate being bonded to the surface of the silicon substrate such that a portion of the second surface of the second substrate forms a top of the planar nanofluidic channel.

2. The method according to claim 1, further comprising forming the region of p-type or n-type doped silicon.

3. The method according to claim 1, wherein the patterned wet oxide etch is an HF etch.

4. The method according to claim 1, further comprising repeating the etching step one or more times.

5. The method according to claim 4, further comprising growing a native oxide layer at the region prior to each etching step.

6. The method according to claim 1, further comprising forming one or more probe contact windows in the second substrate.

7. The method according to claim 1, wherein the second substrate is bonded to the surface of the silicon substrate according to an anodic bonding process.

* * * * *